United States Patent [19]

Dreiling et al.

[11] Patent Number: 5,220,178
[45] Date of Patent: Jun. 15, 1993

[54] APPARATUS AND PROCESS FOR DETECTING THE PRESENCE OF DEFECTS ON A MOVING SHEET OF MATERIAL

[75] Inventors: Mark J. Dreiling; Frankie K. Wood-Black; George A. Moczygemba, all of Bartlesville, Okla.

[73] Assignee: Phillips Petroleum Company, Bartlesville, Okla.

[21] Appl. No.: 810,471

[22] Filed: Dec. 19, 1991

[51] Int. Cl.$^5$ ............................................. G01N 21/88
[52] U.S. Cl. ..................................... 250/572; 356/430
[58] Field of Search ................ 250/571, 572; 356/239, 356/430, 375

[56] References Cited

U.S. PATENT DOCUMENTS

| | | | |
|---|---|---|---|
| 1,988,169 | 1/1935 | Duckwall | 356/239 |
| 3,469,104 | 9/1969 | Hector | 250/219 |
| 3,812,348 | 5/1974 | Lippke | 356/239 |
| 3,890,227 | 6/1975 | Muehlethaler | 209/111.7 |
| 4,226,538 | 10/1980 | Van Beeck | 356/430 |
| 4,501,953 | 2/1985 | Hollinetz | 250/571 |
| 4,692,769 | 9/1987 | Saitoh et al. | 358/106 |
| 4,972,091 | 11/1990 | Cielo et al. | 250/562 |

OTHER PUBLICATIONS

Krueger; Applying Fiber Optics to Photoelectric Switches; Control Engineering; Aug. 1980; pp. 61–62.
"Automatic online monitoring hikes film-resin quality control"; Plastics Compounding; May/Jun. 1991; pp. 84 and 86.

Primary Examiner—David C. Nelms
Assistant Examiner—Que T. Le
Attorney, Agent, or Firm—Ryan N. Cross

[57] ABSTRACT

A defect detection system for the optical inspection of defects in transparent and translucent sheets of materials. The system utilizes the differing optical properties of different defects to distinguish between such defects as fisheye defects, speck defects and scratches.

23 Claims, 4 Drawing Sheets

APPARATUS AND PROCESS FOR DETECTING THE PRESENCE OF DEFECTS ON A MOVING SHEET OF MATERIAL

In one aspect the invention relates to a method of detecting defects in a sheet of material. According to another aspect, the invention relates to an apparatus for detecting defects in a sheet of material.

In the past, defects in transparent and translucent sheets of materials, such as polymer films have been detected by a visual inspection of the film. This visual inspection is a rather subjective test based on the laboratory technician's perceptions and subsequently is prone to errors. Moreover, this visual inspection is mentally and physically fatiguing to the inspector, rendering it difficult to carry out continuous inspection operations. Therefore, there is a need to remove at least one source of human error from the detecting process by doing a computer-aided count of defects.

Inspection processes have been developed utilizing lights and photocells or cameras to detect defects such as those disclosed in U.S. Pat. Nos. 4,226,538 and 4,692,799. However, these inspection systems have been incapable of distinguishing between different types of defects, such as specks, scratches, and fisheyes.

Distinguishing between these different types of defects is important in judging the quality of the sheets. Typically, information on speck and fisheye defects is more important than that on scratches, so that it is desirable to have a system with enhanced response to speck and fisheye defects and that discriminates against scratches. Moreover, a system that not only has an enhanced response to speck and fisheye defects but is also capable of distinguishing between them is desirable.

It is, therefore, an object of the present invention to provide for an improved apparatus and method which produces reproducible data on the kind, number and size of defects in a sheet of transparent or translucent material.

It is a further object of the present invention to provide an improved apparatus and method which can distinguish between fisheye defects and speck defects.

The above objects are realized in an apparatus for detecting the presence of defects in a moving sheet of material, comprising: a light source having a first longitudinal axis and emitting a first emitted light, the longitudinal axis oriented substantially perpendicular to the direction of movement of the moving sheet; first light detecting means for receiving and analyzing the first emitted light after it has passed through the moving sheet; and a background having an edge located between the light source and the moving sheet such that the edge is oriented substantially parallel to the first longitudinal axis so that the background is imaged in any fisheye defects.

According to another aspect of the invention, there is provided a method of detecting defects in a sheet of material comprising the steps of: projecting a beam of light past at least one edge of a background onto the sheet of material so that the beam of light passes through the sheet of material and the background is imaged in any fisheye defects in the sheet of material; collecting the beam of light that passes through the sheet of material; and analyzing the collected beam of light to detect the defects.

The invention will be described hereinafter by way of example with reference to the accompanied drawings wherein.

In distinguishing between different defects it has been discovered that advantage can be taken of the different optical properties of the different types of defects. In transparent and translucent sheet material, typically plastic, fisheye defects typically show up as thick spots in the sheet and they can vary greatly in size. Most often they will appear transparent but on microscopic examination will contain a gel or contaminant at the core of the sheet defect. Because of their transparent or translucent nature the fisheye defects can act as a small optical lens. On the other hand, speck defects usually appear as an opaque particle lodged within the sheet material; however, they can occur in the thick spots and act as lenses. The present invention takes advantage of the optical properties of fisheye defects to enhance the detection of these defects while discriminating against scratches and striations (die marks).

Figure 1:
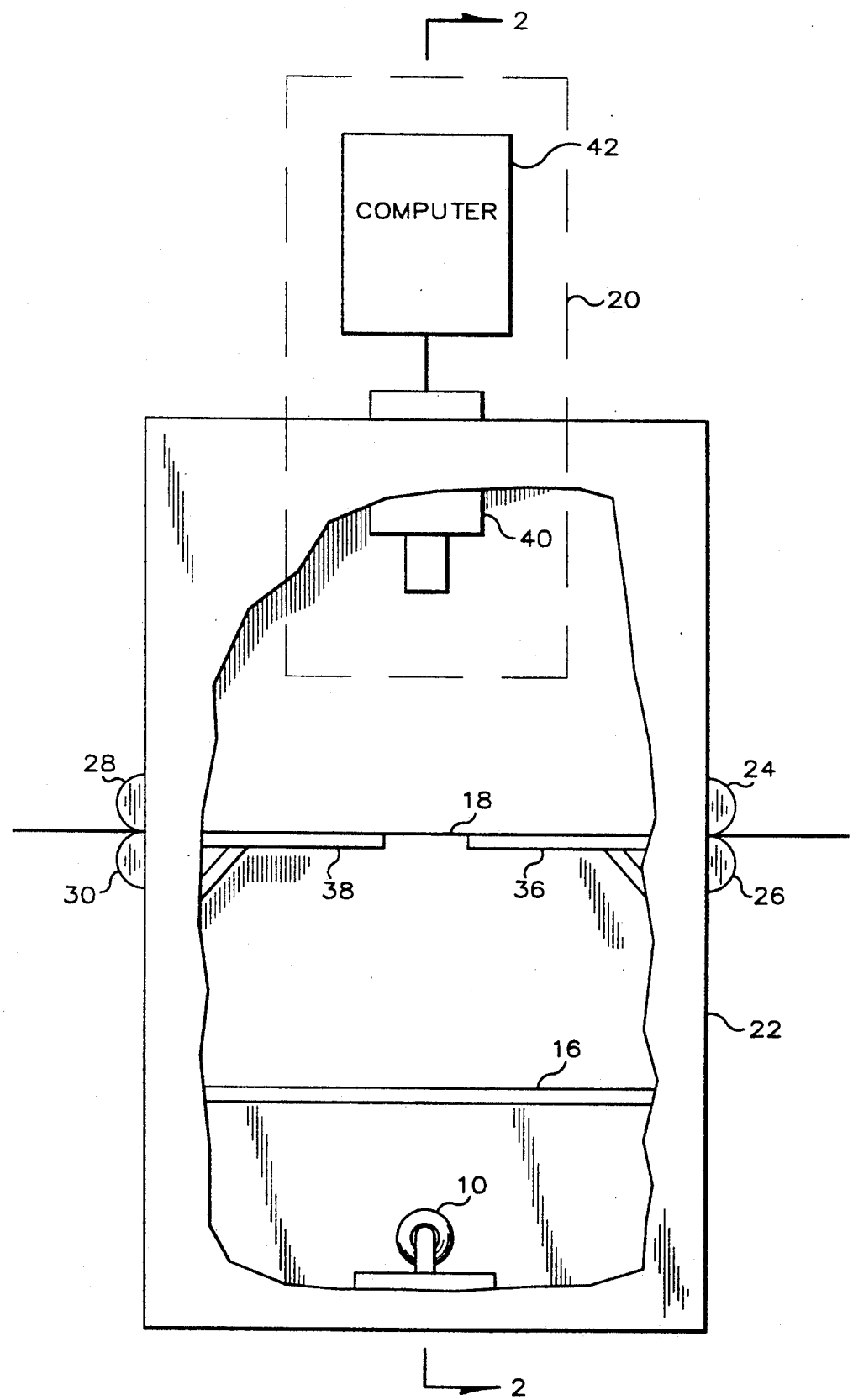
FIG. 1 is a plain view of a device according to the present invention with part of the shielding enclosure removed.
Figures 2, 3, 4:
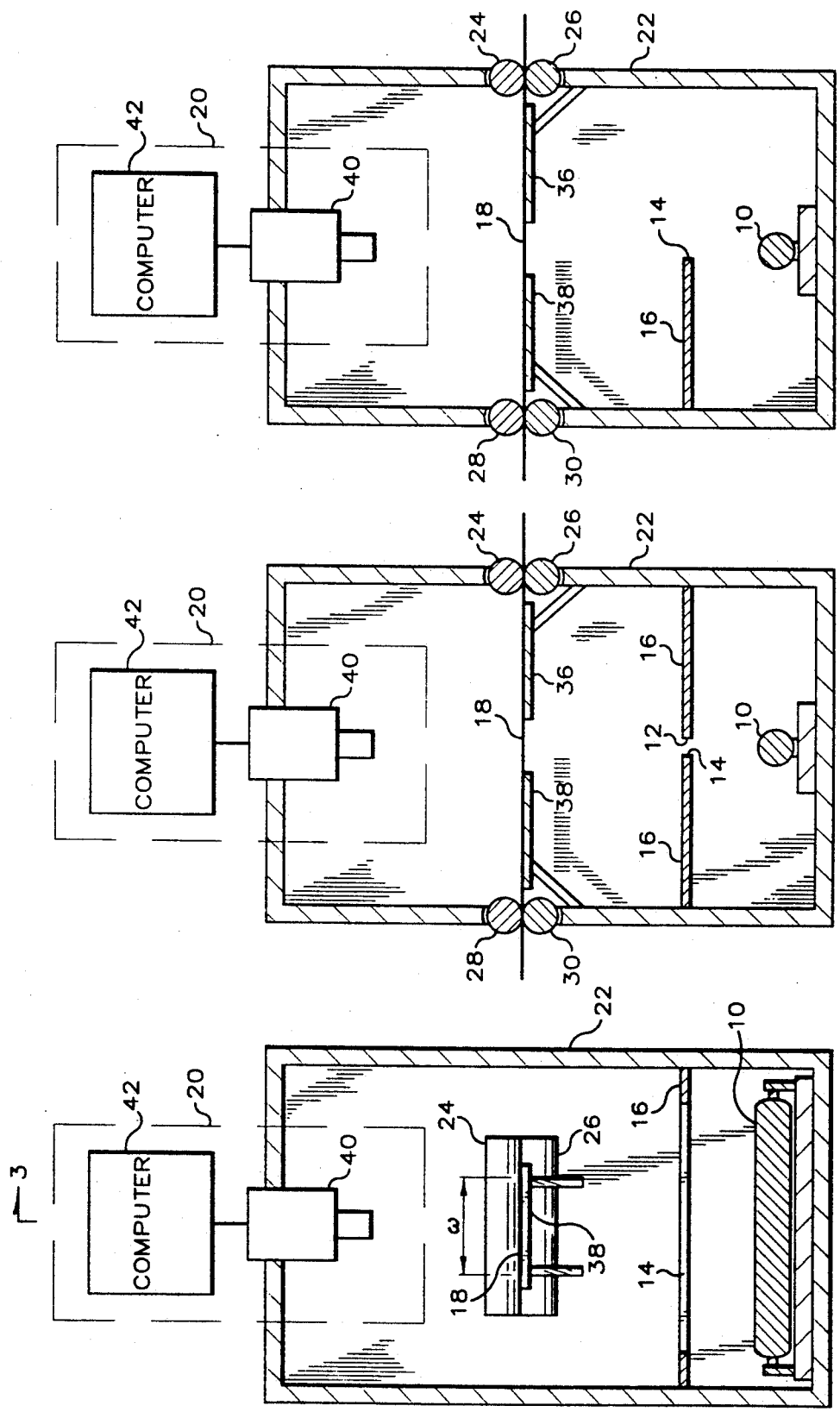
FIG. 2 is a section on line 2—2 of the device of FIG. 1.
FIG. 3 is a section on line 3—3 of the device of FIG. 2.
FIG. 4 is a section view similar to FIG. 3 of an embodiment of the invention utilizing one edge.

Referring to the representations of the optical arrangement in FIGS. 1–3, light from the elongated light source 10 passes through a slit formed by edges 12 and 14, shown in FIG. 3, of the background 16. Edges 12 and 14 are oriented so that the slit formed will have a longitudinal axis substantially perpendicular to the direction of movement as indicated by the arrow in the figures. Elongated light source 10 is oriented so that its longitudinal axis will be substantially perpendicular to the direction of movement and substantially parallel to the slits longitudinal axis. The light then passes through transparent or translucent sheet of material 18 and into a light detecting means 20. Light detecting means 20 can be any suitable means for receiving and analyzing light. As shown in FIGS. 1–3, light detecting means 20 includes camera 40, which serves as an optical means and a light processing means, and computer 42, which serves as a signal processing means.

The optical arrangement, including light source 10, background 16 and a portion of camera 40, is housed in a shielding enclosure represented by box 22. Rollers 24 and 26 are engagingly mounted on one side of box 22, and rollers 28 and 30 are engagingly mounted on the opposite side of box 22. Rollers 24, 26, 28, and 30 serve to guide sheet 18 and can also be rotated by a suitable driving means (not shown) so that they serve to move film 18 through box 22, preferably at a constant rate. Thus, rollers 24 and 26 could be rotated such that they would pull sheet 18 through box 22. Rollers 24, 26, 28 and 30 can have ridges or other means which help to guide film 18 through box 22. Sheet 18 can be supported inside box 22 by a suitable means such as support shelves 36 and 38.

Referring now to FIG. 4, there is shown an alternative embodiment of the invention in a perspective similar to FIG. 3. In FIG. 4, only one edge 14 is utilized in the invention instead of the two-edge slit of FIGS. 1-3.

In operation the apparatus of FIGS. 1-4, detects defects by passing light from light source 10 past edges 12 and 14 of background shelf 16 through sheet 18 and to light detecting means 20 where the presence of defects is recorded. It is believed that the fisheye defects and speck defects are observed because they act as optical lenses and images background 16; however, some speck defects could be observed due to absorption of light. Preferably, background 16 is dark to produce a dark image in the fisheye defects. Most preferably background 16 is black. The fisheye defects become more visible if background 16 is placed closer to the light source than the film. Thus, to camera 40 the speck defects and fisheye defects will appear darker than the surrounding sheet, typically they will appear as gray or black spots on a lighter field. The preferred distances between the light detecting means, the film, the background, and the light source depend on the equipment and film used, but is readily determined by one skilled in the art.

If edges 12 and 14 of background 16 are long with respect to the width of sheet 18, shown in FIG. 2 as W, then the interference caused by any striations in the film that run parallel to the direction of movement imaging the background is minimized. Defects such as scratches are only slightly visible and caused little problems. Under this condition a threshold light level can be set so that the light detecting means does not detect striations or scratches but still detects substantially all the fisheye defects and speck defects. Typically, an arrangement with the edges more than about 4 times the width is desirable. Preferably, the edges will be more than 6 times the width.

Figure 5:
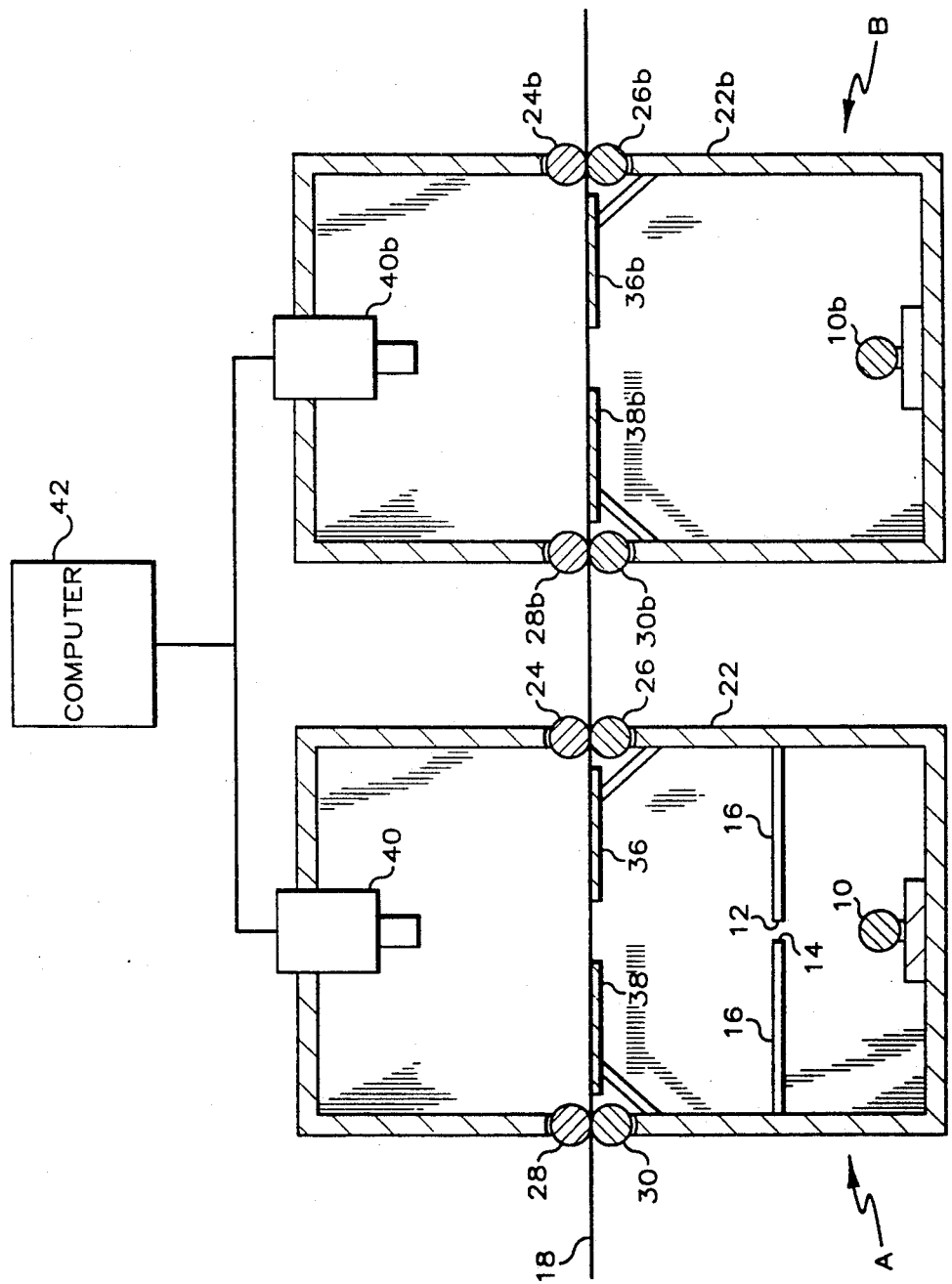
FIG. 5 is a section view similar to FIG. 3 of an embodiment of the invention utilizing a first and second detection stage.

FIG. 5 shows a further embodiment with two enclosed units A and B. Units A and B form a first and second detection stage, respectively, so that this embodiment is capable of distinguishing between fisheye defects and speck defects. Film 18 first passes through enclosed unit A which is of the type previously described in FIGS. 1-3. Then film 18 is passed through enclosed unit B which is similar to enclosed unit A except that background shelf 16 is absent. Thus, unit B contains its own light source 10b, rollers 24b, 26b, 28b and 30b, shielding enclosure 22b, shelves 36b and 38b, and camera 40b. This apparatus allows for a comparison of the process signals received from the two enclosed units in signal processing device 42 to enable a separate analysis of fisheye defects.

Figure 6:
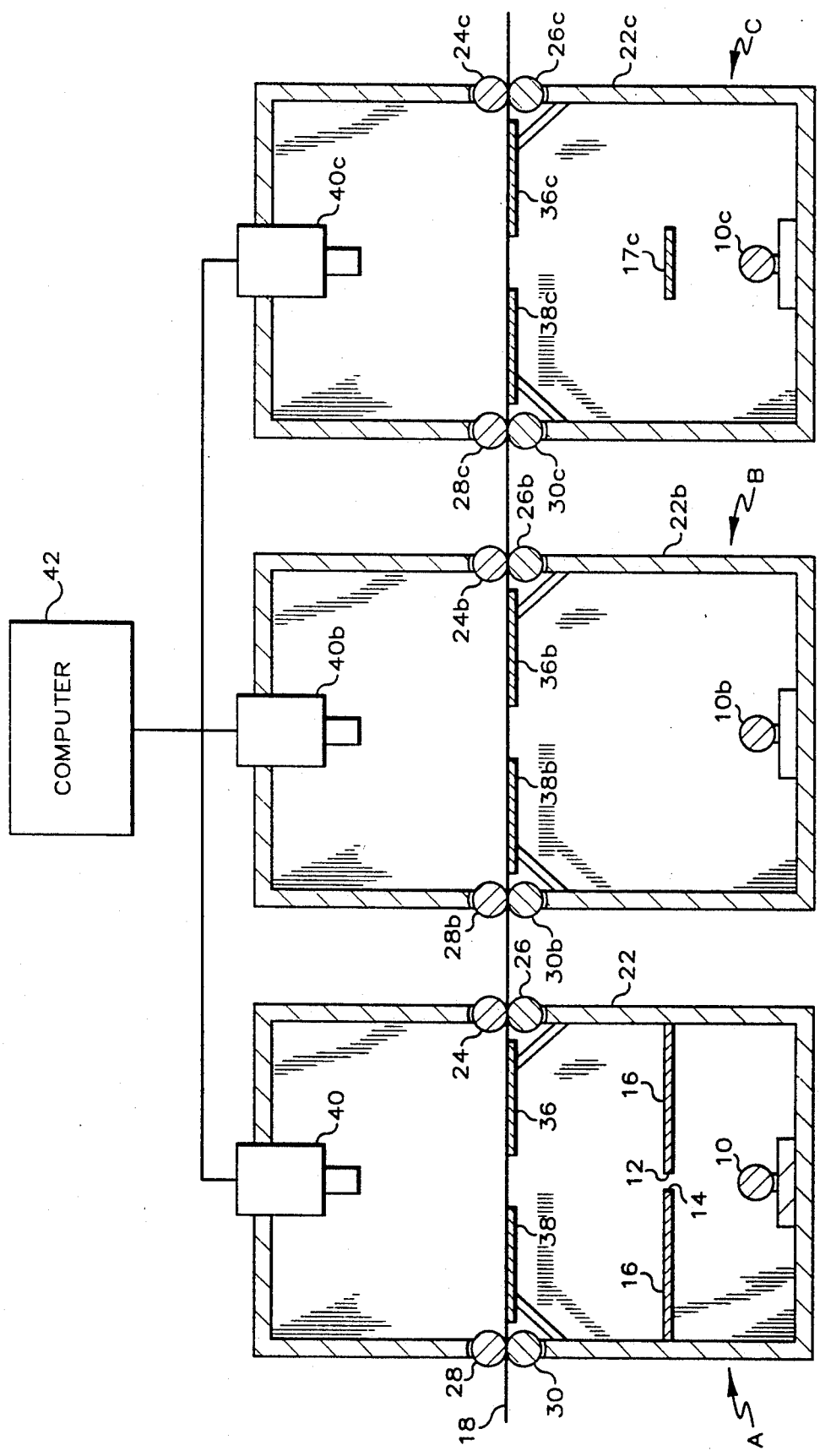
FIG. 6 is a section view similar to FIG. 3 of an embodiment of the invention utilizing a first, second, and third detection stage.

Unit B of the apparatus as illustrated in FIGS. 5 and 6 contains no background shelf 16 and, subsequently, fisheye defects do not show up as dark or gray spots. It is believed that fisheye defects do not show up as dark or gray spots because they have no background to image and, therefore, transmit or image light from light source 10b. Speck defects, on the other hand, also have no background to image but still absorb light and can be observed as gray or black spots. In unit B, therefore, only speck defects are recorded by light detecting device 20. Signals from camera 40b are processed in signal processing device 42 where the size, location and number of speck defects are recorded and can be compared with the size, location and number of speck defects and fisheye defects recorded from enclosed unit A. Thus, the size, location and number of fisheye defects can be determined.

FIG. 6 shows still another embodiment of the invention utilizing three enclosed units A, B and C. Units A, B and C form a first, second and third detection stage, respectively, so that this embodiment is capable of distinguishing between fisheye defects, speck defects, and scratches. Film 18 is passed through units A and B which are the type previously described in FIG. 5. Then film 18 is passed through enclosed unit C, which also contains its own light source 10c, rollers 24c, 26c, 28c and 30c, shielding enclosure 22c, shelves 36c and 38c, and camera 40c. However, shelf 16 is replaced with strip 17c running parallel to the longitudinal axis of elongated light source 10c, perpendicular to the direction of movement as shown by the arrow and in confronting relation to both light source 10c and camera 40c. Strip 17c preferably just covers the camera's field of view. Thus, strip 17c allows only light at an acute angle to the film to be incident on the portion of the film being observed. Unit C produces a negative image from that produced in units A and B, having bright scratches, fisheye defects and speck defects on a dark background. It is believed that in the configuration of Unit C the fisheye defects act as lenses and divert the light that comes around strip 17c to the camera, the scratches provide a way for the light that is trapped inside the sheet, by total internal reflection, to exit the sheet, and the speck defects appear light due to local distortion in the sheet material, and thus, they allow light to escape, as well as image the light from the sides of the strip. Thus, the defects appear brighter than the surrounding sheet material. Signals from camera 40c are processed in signal processing device 42 where the size, location and number of speck defects, fisheye defects and scratches are recorded and can be compared with the size, location and number of speck defects and fisheye defects obtained from enclosed units A and B to determine the type of each defect. Therefore this apparatus allows for comparison of the process signals received from all three enclosed units and is able to separately distinguish fisheye defects, speck defects and scratches.

Suitable distances between film and camera, film and light source, and film and background as well as the width of the film and length of the background edge can be readily determined from the description above by one skilled in the art.

In light detecting device 20, light is detected in camera 40 and changed into an electrical signal which is transmitted to a signal processing device, such as computer 42. In computer 42, the signal is analyzed to determine the size, number, and location of gray or black spots that appear on the light field. The information determined by the computer can then be stored for latter reference, further analysis, or displayed on a plotter or video display terminal.

The above-described apparatuses are useful for seeing several distinct kinds of defects in transparent and translucent sheets, preferably ones produced from plastic resins, such as poly(arylene sulfide); polyethylene, and polypropylene. In such sheets it is often desirable to detect both the fisheyes and black specks without interference by scratches or striations. The examples will further illustrate how the apparatus can detect each of the major defects.

EXAMPLE I

A transparent sheet of 10 mil poly(phenylene sulfide) film, marketed as Ryton ® by Phillips Petroleum Company, 36 inches long and 2 inches wide is analyzed for speck defects and fisheye defects. The Fisheye Defect Detector is set up for normal operation. The setup comprises a Sierra Scientific video camera interfaced to a Macintosh II computer using a Scion Corp. Interface board. The camera is set up with the lens facing in a downward position approximately 7.5 inches away from the film and approximately 13.0 inches from the light source.

The film feed mechanism is located above the light source. The light source is a Phillips Electronics "Earth Light" fluorescent 110 volt light bulb with diffuser plates arranged to obtain a uniform light intensity. Two parallel edges arranged 0.028 inches apart as an aperture and are placed approximately 5.5 inches behind the film and in front of the light source. The distances between the camera, film and aperture are not critical.

The public domain computer program called Image 1.37 available on the Compuserve network is used to collect and analyze data from the signal of the camera. The program manual and source code are available in its current version (1.41 n) on the Compuserve network. The imagery portion of the public domain program is used to image the defects. Additional code is added to turn the film roller motor on/off and to analyze the data collected, and unused portions of the program are deleted. The modified program works successfully on the MacIntosh II series of computers.

The system is then calibrated to obtain reproducible film grading. It distinguishes 256 grey levels between white and black, with level 0 assigned to white and level 255 assigned to black. The calibration is done by adjusting the camera lens aperture to obtain a light level of 30 in the absence of a film. It is assumed that there are no significant variations in the thickness of the test films.

The film is then fed through the film rollers and positioned between the light source and camera lens. The program and film motor are started at the same time. A short length of film is measured to determine the average grey level seen by the camera in the presence of the film. This average grey level from all pixels in the field of view is called the "background" and is typically a grey level of 70. A threshold grey level used to detect defects is typically set about 60 levels higher, to 130 in this case. During the run, only the pixels that are measured above this threshold level will be identified with defects. The video camera collected visual data on the area (a 32 pixels wide and 400 pixels long frame) of the slit. Each pixel is checked to see if it is above the threshold level. If it is, the position of the pixel is recorded to computer memory. The next frame is taken by the camera and the process is repeated. The raw data is stored until the next sample is run. Once the run is completed, the total number of pixels recorded will appear on the computer screen.

After the film is scanned and the raw data collected, the program scans the data and detects clusters of the recorded pixels. The number of pixels in each cluster is recorded as the defect size and the center of gravity is recorded as the defect position on the film. The total number of clusters is printed to the screen when this part of the program has been completed. A third and final file is created of defects larger than 30 to 40 pixels. The data reduced down to 144 fisheye and black speck defects that are larger than 30 pixels in the (36 inches long and 2 inches wide) film strip; thus, the system detected an average of 2 defects per square inch.

EXAMPLE II

Removal of the two parallel dark edges in the same system used in Example I provides a means for measuring the black specks. The specks are observed by the absorption of light from the light source.

The same procedure and film is used as in Example I except the two parallel edges are removed. 75 speck defects are detected. The data is then further analyzed to compare with the data in Example I. From this analysis it is determined that 69 fisheye defects are present.

The above examples illustrate that the present invention provides an apparatus and method for producing reproducible data on defects in transparent and translucent sheets of materials in a manner that is capable of distinguishing between fisheye defects, speck defects while discriminating against scratches and striations.

Various modifications and alterations of this invention will become apparent to those skilled in the art without departing from the scope and spirit of this invention, and it should be understood that the foregoing discussion, embodiments and examples are merely set forth for illustrative purposes and should not unduly limit this invention.

That which is claimed is:

1. An apparatus for detecting the presence of defects in a moving sheet of material, wherein said defects comprise at least one fisheye defect and at least one speck defect, comprising:
    a first elongated light source having a first longitudinal axis and emitting a first emitted light, said first longitudinal axis oriented substantially perpendicular to the direction of movement of said moving sheet;
    first light detecting means for receiving and analyzing said first emitted light after it has passed through said moving sheet; and
    a background having at least one edge, said background located between said first elongated light source and said moving sheet such that said edge is oriented substantially parallel to said first longitudinal axis, and so that said background is imaged in said fisheye defects.

2. An apparatus according to claim 1 further comprising:
    a second elongated light source having a second longitudinal axis and emitting a second emitted light, said second longitudinal axis oriented substantially perpendicular to the direction of movement of said moving sheet;
    second light detecting means for receiving and analyzing said second emitted light after it has passed through said moving sheet so that said second emitted light is imaged in said fisheye defects and said speck defects prevent a portion of said second emitted light from reaching said second light detecting means; and
    means to compare the analysis of said first emitted light and the analysis of said second emitted light.

3. An apparatus according to claim 2 wherein said defects further comprise at least one scratch and further comprising:
    a third elongated light source having a third longitudinal axis and emitting a third emitted light, said third longitudinal axis oriented substantially perpendicular to the direction of movement of said moving sheet;

third light detecting means for receiving and analyzing said third emitted light after it has passed through said moving sheet; and a strip located between said third elongated light source and said moving sheet and between said third light source and said third light detecting means and oriented substantially parallel to said third longitudinal axis, such that said third light detecting means detects said scratches, said fisheye defects, and said speck defects as brighter than the rest of said moving sheet;

means to compare the analysis of said first emitted light, the analysis of said second emitted light, and the analysis of said third emitted light.

4. An apparatus according to claim 1 wherein said moving sheet has a width parallel to said longitudinal axis and said edge of said background is longer than the width of said moving sheet.

5. An apparatus according to claim 1 wherein said background is dark.

6. An apparatus according to claim 1 wherein said light detecting means comprises: optical means for collecting light emitted from said first elongated light source and having passed through said moving sheet; light processing means for detecting said light collected by said optical means and converting said detected light into a time-resolved electrical signal; and signal processing means for detecting the presence of defects in said moving sheet.

7. An apparatus according to claim 1 further comprising a shielding enclosure for enclosing said first elongated light source, at least a portion of said first light detecting means, and said background so that only light from said first elongated light source illuminates said moving sheet.

8. An apparatus according to claim 1 wherein said background has a pair of edges forming a slit and said background is located between said first elongated light source and said moving sheet such that said slit is in confronting relation with both said light source and said first light detecting means such that said background is imaged in said fisheye defect.

9. An apparatus according to claim 8 wherein said moving sheet has a width parallel to said longitudinal axis, and said slit is longer than the width of said moving sheet.

10. An apparatus according to claim 9 wherein:
said background is dark; and
said first light detecting means comprises a first optical means for collecting light emitted from said first elongated light source and having passed through said moving sheet, a first light processing means for detecting said light collected by said first optical means and converting said thus detected light into a time-resolved electrical signal, and a signal processing means for detecting the presence of defects in said moving sheet;
and further comprising:
a shielding enclosure for enclosing said first elongated light source, said first optical means, and said background so that only light passing through said slit illuminates said moving sheet and is received in said first optical means.

11. An apparatus for detecting the presence of defects in a moving sheet of material wherein said defects comprise fisheye defects, speck defects and scratches, comprising:

a first elongated light source having a first longitudinal axis and emitting a first emitted light, said first longitudinal axis oriented substantially perpendicular to the direction of movement of said moving sheet;

first optical and light processing means for collecting first emitted light after it has passed through said moving sheet, and for converting said collected first emitted light into a first time resolved electrical signal;

a background having at least one edge, said background located between said first optical and light processing means and said moving sheet such that said edge is oriented substantially parallel to said first longitudinal axis so that said background is imaged in said fisheye defects and said speck defects prevent a portion of said first emitted light from reaching said first optical and light processing means;

a first shielding enclosure for enclosing said first elongated light source, at least a portion of said first optical and light processing means, and said background so that only first emitted light illuminates said moving sheet and is received in said first optical and light processing means;

means to pass said moving sheet through said first shielding enclosure;

a second elongated light source having a second longitudinal axis and emitting a second emitted light, said second longitudinal axis oriented substantially perpendicular to the direction of movement of said moving sheet;

a second optical and light processing means for collecting second emitted light after it has passed through said moving sheet so that light is image in said fisheye defects and said speck defects prevent a portion of said second emitted light from reaching said second optical and light processing means, and for converting said collected second emitted light into a second time resolved electrical signal;

a second shielding enclosure for enclosing said second elongated light source and at least a portion of said second optical light processing means so that only light from said second elongated light source is received in said second optical and light processing means;

means to pass said moving sheet through said second shielding enclosure;

a third elongated light source having a third longitudinal axis and emitting a third emitted light, said third longitudinal axis oriented substantially perpendicular to the direction of movement of said moving sheet;

third optical and light processing means for collecting said third emitted light after it has passed through said moving sheet and for converting said collected third emitted light into a third time resolved electrical signal;

a strip located between said third elongated light source and said moving sheet and between said third elongated light source and said third optical and light processing means and oriented substantially parallel to said third longitudinal axis, such that said third optical and light processing means detects scratches, fisheye defects, and speck defects as brighter than the rest of the moving sheet;

a third shielding enclosure for enclosing said third light source, at least a portion of said third optical and light processing means, and said strip so that only third emitted light passing around said strip illuminates said moving sheet and is received in said third optical and light processing means;

means to pass said moving sheet through said third shielding enclosure;

signal processing means, operationally connected to said first optical and light processing means, said second optical and light processing means and said third optical and light processing means, for analyzing and comparing said first time resolved electrical signal, said second time resolved electrical signal, and said third time resolved electrical signal for determining the kind, location, number and size of defects in said moving sheet.

12. A method of detecting defects in a sheet of material, wherein said defects comprise fisheye defects and speck defects, comprising the steps of:

(a) projecting a first beam of light post at least one edge of a background onto a portion of said sheet of material so that said first beam of light passes through said sheet of material and said background is imaged in said fisheye defects in said sheet of material;

(b) collecting said first beam of light after it passes through said portion of said sheet of material; and (c) analyzing said thus collected first beam of light to detect said defects.

13. A method according to claim 12 further comprising moving said sheet of material during steps (a), (b) and (c) so that different portions of said sheet are examined.

14. A method according to claim 13 wherein said at least one edge of said background is oriented so that it is substantially perpendicular to said direction of movement and substantially perpendicular to said beam of light.

15. A method according to claim 14 wherein said sheet has a width substantially parallel to said at least one edge and said edge is longer than the width of said sheet.

16. A method according to claim 12 further comprising shielding said steps (a) and (b) from light other than said first beam of light.

17. A method according to claim 12 further comprising:

(d) projecting a second beam of light onto said portion of said sheet of material so that said beam of light passes through said portion of said sheet of material and said fisheye defects image said second beam of light;

(e) collecting said second beam of light after it passes through said portion of said sheet of material;

(f) analyzing said thus collected second beam of light to detect opaque particles in said sheet of material; and (g) comparing said analysis of said first beam of light and said analysis of said second beam of light to determine the amount of fisheye defects.

18. A method according to claim 17 wherein said sheet of material has two surfaces, and further comprising:

(h) projecting a third beam of light onto said portion of said sheet of material so that said light is incident onto said portion of said sheet of material at an acute angle to at least one of said surfaces of said sheet of material;

(i) collecting light from said third beam of light after it passes through said portion of said sheet of material;

(j) analyzing said thus collected light from said third beam of light; and (k) comparing said analysis of said first beam of light, said analysis of said second beam of light and said analysis of said third beam of light to determine the kind, size, number and location of defects.

19. A method according to claim 12 wherein said background has a pair of edges forming a slit; said slit is positioned so that said first beam of light passes through said slit.

20. A method according to claim 19 wherein said sheet has a width parallel to said slit and said slit is longer than the width of said film.

21. A method according to claim 20 wherein said sheet of material has two surfaces and further comprising:

(d) projecting a second beam of light onto said sheet of material so that said beam of light passes through said portion of said sheet of material and said fisheye defects image said second beam of light;

(e) collecting said second beam of light after it passes through said portion of said sheet of material;

(f) analyzing said thus collected second beam of light to detect opaque particles in said sheet of material;

(g) projecting a third beam of light onto said sheet of material so that said light is incident onto said portion of said sheet of material at an acute angle to at least one of said surfaces of said sheet of material;

(h) collecting light from said third beam of light after it passes through said portion of said sheet of material;

(i) analyzing said thus collected light from said third beam of light; and (j) comparing said analysis of said first beam of light, said analysis of said second beam of light and said analysis of said third beam of light to determine the kind, size, number and location of defects.

22. A method according to claim 21 further comprising shielding said steps (a) and (b) from light other than said first beam of light; shielding said steps (d) and (e) from light other than said second beam of light; and shielding said steps (g) and (h) from light other than said third beam of light.

23. A method according to claim 22 further comprising moving said sheet of material during said steps (a)–(j) so that different portions of said sheet are examined and wherein said slit is oriented so that it is substantially perpendicular to the direction of said movement.

* * * * *